United States Patent [19]

Lautenschläger et al.

[11] Patent Number: 4,504,479
[45] Date of Patent: Mar. 12, 1985

[54] 6-{5-[ω-(1-IMIDAZOLYL)-ALKYL]-THIEN-2-YL}-3-OXO-2,3,4,5-TETRAHYDRO-PYRIDAZINES AND ACID ADDITION SALTS THEREOF AND A PROCESS FOR THE TREATMENT OF INFLAMMATORY ATHEROSCLEROTIC AND THROMBO-EMBOLIC, ILLNESSES IN HUMANS

[75] Inventors: Hans-Heiner Lautenschläger, Pulheim-Stommeln; Gerd Hilboll, Cologne; Hugo Friehe, Erftstadt-Lechenich; Josef P. Löhr, Hilden, all of Fed. Rep. of Germany

[73] Assignee: A. Nattermann & Cie GmbH, Cologne, Fed. Rep. of Germany

[21] Appl. No.: 397,090

[22] Filed: Jul. 12, 1982

[30] Foreign Application Priority Data

Jul. 31, 1981 [DE] Fed. Rep. of Germany ....... 3130252

[51] Int. Cl.³ .................... C07D 237/06; A61K 31/50
[52] U.S. Cl. .................................. 514/252; 544/238; 544/239
[58] Field of Search ................ 544/238; 424/250, 251

[56] References Cited

U.S. PATENT DOCUMENTS 4,057,634 11/1977 Winkelmann et al. .............. 544/238
4,353,905 10/1982 Sircar et al. ........................ 424/250

FOREIGN PATENT DOCUMENTS 2031408 4/1980 United Kingdom .

Primary Examiner—Nicholas S. Rizzo
Attorney, Agent, or Firm—Pearne, Gordon, Sessions, McCoy, Granger & Tilberry

[57] ABSTRACT

The invention relates to new 6-{5-[ω-(1-imidazolyl)-alkyl]-thien-2-yl}-3-oxo-2,3,4,5-tetrahydro-pyridazines having the general formula I

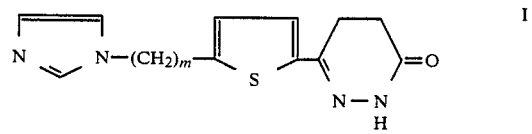

and acid addition salts thereof and to a process for the treatment of inflammatory, atherosclerotic and thrombo-embolic diseases especially in humans.

15 Claims, No Drawings

6-{5-[ω-(1-IMIDAZOLYL)-ALKYL]-THIEN-2-YL}-3-OXO-2,3,4,5-TETRAHYDRO-PYRIDAZINES AND ACID ADDITION SALTS THEREOF AND A PROCESS FOR THE TREATMENT OF INFLAMMATORY ATHEROSCLEROTIC AND THROMBO-EMBOLIC, ILLNESSES IN HUMANS

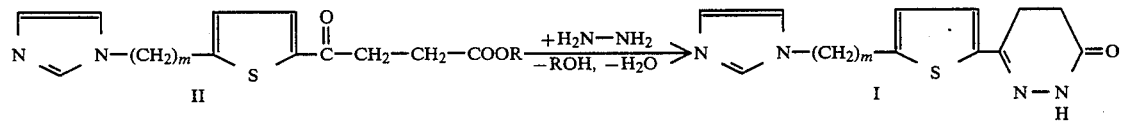

The present invention relates to new 6-{5-[ω-(1-imidazolyl)-alkyl]-thien-2-yl}-3-oxo-2,3,4,5-tetrahydro-pyridazines and acid addition salts thereof, to a process for the preparation of these compounds, and to their use as the active compound in medicaments, in particular for the treatment of inflammatory and thrombo-embolic illnesses. The 6-{5-[ω-(1-imidazolyl)-alkyl]-thien-2-yl}-3-oxo-2,3,4,5-tetrahydro-pyridazines according to the invention correspond to the general formula I

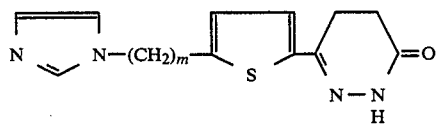

wherein m is an integer from 1 to 12, in particular 1 to 5; acid addition salts of the formula I are also included. Acid addition salts are, in particular, pharmaceutically useful, non-toxic acid addition salts with inorganic acids, for example hydrochloric acid, hydrobromic acid, sulphuric acid or phosphoric acid, or with organic acids, such as appropriate carboxylic acids, for example acetic acid, propionic acid, oxalic acid, malonic acid, glycolic acid, succinic acid, maleic acid, fumaric acid, malic acid, tartaric acid, citric acid, benzoic acid or cinnamic acid.

The compounds of the present invention have valuable pharmacological properties. On the one hand, they are distinguished by their powerful influence on the metabolism of arachidonic acid, and on the other hand they display an antagonistic action in respect of some physiological processes controlled by PAF (platelet activating factor). The compounds according to the invention therefore or moreover have a powerful antithrombotic, antiatherosclerotic and antirheumatic activity. In addition, the compounds of the general formula I have a favourable influence on asthmatic complaints as well as blood pressure-regulating properties. They can be used, in particular, for the treatment of inflammatory, atherosclerotic and thrombo-embolic illnesses, especially in humans.

The substances according to the invention are prepared by reacting a 4-{5-[ω-(1-imidazolyl)-alkyl]-thien-2-yl}-4-oxo-butyric acid or an ester of the formula II with hydrazine or its hydrate or salts, such as the hydrochloride, hydrosulphate and the like, in aqueous, aqueous-alcoholic or alcoholic media or in inert organic solvents, such as, for example, toluene or mixtures thereof with water or alcohol, at temperatures of from 0° to 150° C., preferably in ethanol or water. If appropriate, the reaction can be catalysed by acids, which can be used in the form of their hydrazinium salts, or by bases, such as, for example, alkaline earth metal oxides.

The reaction is illustrated by the following equation:

Possible starting compounds of the formula II are, in particular: 4-[5-(1-imidazolylmethyl)-thien-2-yl]-4-oxo-butyric acid and $C_{1-6}$-alkyl esters thereof; 4-{5-[2-(1-imidazolyl)-ethyl]-thien-2-yl}-4-oxo-butyric acid and $C_{1-6}$-alkyl esters thereof; 4-{5-[3-(1-imidazolyl)-propyl]-thien-2-yl}-4-oxo-butyric acid and $C_{1-6}$-alkyl esters thereof; 4-{5-[4-(1-imidazolyl)-butyl]-thien-2-yl}-4-oxo-butyric acid and $C_{1-6}$-alkyl esters thereof; 4-{5-[5-(1-imidazolyl)-pentyl]-thien-2-yl}-4-oxo-butyric acid and $C_{1-6}$-alkyl esters thereof; 4-{5-[6-(1-imidazolyl)-hexyl]-thien-2-yl}-4-oxo-butyric acid and $C_{1-6}$-alkyl esters thereof; 4-{5-[7-(1-imidazolyl)-heptyl]-thien-2-yl}-4-oxo-butyric acid and $C_{1-6}$-alkyl esters thereof; 4-{5-[8-(1-imidazolyl)-octyl]-thien-2-yl}-4-oxo-butyric acid and $C_{1-6}$-alkyl esters thereof; 4-{5-[9-(1-imidazolyl)-nonyl]-thien-2-yl}-4-oxo-butyric acid and $C_{1-6}$-alkyl esters thereof; 4-{5-[10-(1-imidazolyl)-decyl]-thien-2-yl}-4-oxo-butyric acid and $C_{1-6}$-alkyl esters thereof; 4-{5-[11-(1-imidazolyl)-undecyl]-thien-2-yl}-4-oxo-butyric acid and $C_{1-6}$-alkyl esters thereof and 4-{5-[12-(1-imidazolyl)-dodecyl]-thien-2-yl}-4-oxo-butyric acid and $C_{1-6}$-alkyl esters thereof.

The starting compounds of the formula II are prepared by processes which are known per se: 1-(ω-thienylalkyl)-imidazoles are prepared by alkylation of imidazole with the corresponding ω-halogenoalkylthiophene, if appropriate with the addition of an organic solvent, such as, for example, dimethylformamide, and with the possible use of an auxiliary base, such as, for example, sodium hydride (British Patent Application No. 2,031,408). The 1-(ω-thienylalkyl)-imidazoles are reacted with a succinic acid alkyl ester chloride, with the addition of an organic solvent, such as, for example, 1,2-dichloroethane, nitrobenzene or carbon disulphide, using a Friedel-Crafts catalyst, such as, for example, aluminium chloride, by processes familiar to the expert (Houben-Weyl, Methoden der organischen Chemie (Methods of Organic Chemistry), Volume 7/2a, page 257 et seq.) to give the 4-{5-[ω-(1-imidazolyl)-alkyl]-thien-2-yl}-4-oxo-butyric acid alkyl esters.

The acid addition salts of compounds of the formula I with inorganic or organic acids can be prepared by mixing the imidazolyl compounds on which they are based with the corresponding acids in aqueous, aqueous-organic (for example alcohol/water) or organic media, such as, for example, alcohols, alcohol/ether mixtures or ether/petroleum ether mixtures, at temperatures between 0° and 100° C.

The present invention also relates to pharmaceutical products which contain compounds of the formula I or pharmaceutically usable acid addition salts of these compounds. The pharmaceutical products according to the invention are products for enteral, such as oral or rectal, or parenteral administration which contain the pharmaceutical active compounds by themselves or together with a customary, pharmaceutically usable excipient.

Advantageously, the pharmaceutical formulation of the active compound is in the form of individual doses appropriate for the desired administration, such as, for example, tablets, coated tablets, capsules, suppositories, granules, solutions, emulsions or suspensions.

The dosage of the compound is usually between 1 and 500 mg per dose, preferably between 5 and 150 mg per dose, and can be administered once or several times, preferably two to three times, daily. The preparation of the compounds according to the invention is illustrated in more detail by the examples which follow. The melting points given were measured with a Büchi 510 melting point determination apparatus, and are given in °C. and are uncorrected. The IR spectra were recorded with a Perkin Elmer 257 apparatus and the mass spectra with a Varian MAT-311-A (70 eV) apparatus.

EXAMPLE 1

6-[5-(1-Imidazolylmethyl)-thien-2-yl]-3-oxo-2,3,4,5-tetrahydro-pyridazine (a) From 4-[5-(1-imidazolylmethyl)-thien-2-yl]-4-oxo-butyric acid methyl ester.

A mixture of 7.3 g of the ester, 0.2 g of barium oxide, 1.3 g of hydrazine hydrate and 30 ml of ethanol is stirred at 0° C. for 10 minutes and then at room temperature for 20 hours, and is subsequently heated under reflux for 4 hours. After the mixture has been cooled, the solvent is stripped off and the residue is taken up in water and extracted with chloroform. The chloroform phase is washed with water, dried over $Na_2SO_4$ and concentrated. The residue is purified by repeated recrystallisation from ethanol.

Yield: 2.72 g, melting point: 186°
IR (in KBr): 1,670 $cm^{-1}$
MS [m/e]: 260 (M+, 22%), 193 (100%), 151 (15%), 122 (39%)

(b) From 4-[5-(1-imidazolylmethyl)-thien-2-yl]-4-oxo-butyric acid.

15 g of the acid are suspended in 50 ml of water, 3.4 g of hydrazine hydrate are added and the mixture is stirred at 90° C. for 2 hours. After the mixture has been cooled, it is extracted with chloroform and the chloroform phase is washed with water, dried over $Na_2SO_4$ and concentrated to dryness.

Yield: 10.9 g, melting point: 187°–188° C.

PREPARATION OF THE STARTING COMPOUND

4-[5-(1-Imidazolylmethyl)-thien-2-yl]-4-oxo-butyric acid methyl ester 19.5 g of succinic acid methyl ester chloride and then a solution of 20 g of 1-(thien-2-ylmethyl)-imidazole in 200 ml of 1,2-dichloroethane are added dropwise to a suspension of 53.5 g of aluminium chloride in 240 ml of 1,2-dichloroethane, whilst cooling with ice. The mixture is then stirred at 50° C. for 3 hours. After it has been cooled, the reaction mixture is stirred into a mixture of 147.3 g of ethylenediaminetetraacetic acid and 500 g of ice and is brought to about pH 8 by addition of dilute sodium hydroxide solution. The phases are separated and the organic phase is dried over $Na_2SO_4$ and concentrated. Extraction of the residue by stirring with hexane gives colourless crystals.

Yield: 26.3 g, melting point: 69°–70° C.
IR (in KBr): 1,720 and 1,655 $cm^{-1}$
MS [m/e]: 278 (M+, 32%), 247 (17%), 211 (100%)

4-[5-(1-Imidazolylmethyl)-thien-2-yl]-4-oxo-butyric acid

A mixture of 4.17 g of 4-[5-(1-imidazolylmethyl)-thien-2-yl]-4-oxo-butyric acid methyl ester, 0.8 g of sodium hydroxide and 20 ml of methanol is stirred at room temperature for 8 hours. The solvent is then stripped off and the residue is taken up in water. The solution is extracted several times with chloroform, and the chloroform phase is discarded. The aqueous solution is brought to about pH 7 with dilute hydrochloric acid and is concentrated to dryness. The residue is purified by column chromatography (silica gel/$CHCl_3$/methanol).

Yield: 1.4 g, melting point: 203°–205° C. (decomposition)
IR (in KBr): 1,700 and 1,660 $cm^{-1}$
MS [m/e]: 264 (M+, 1.5%), 220 (6%), 197 (100%), 192 (27%), 151 (40%), 124 (26%), 97 (41%)

EXAMPLE 2

6-{5-[2-(1-Imidazolyl)-ethyl]-thien-2-yl}-3-oxo-2,3,4,5-tetrahydro-pyridazine 4.2 g of 4-{5-[2-(1-imidazolyl)-ethyl]-thien-2-yl}-4-oxo-butyric acid are suspended in 10 ml of water, 0.8 g of hydrazine hydrate are added and the mixture is stirred at 90° C. for 2 hours. After the mixture has been cooled, it is extracted with chloroform. The chloroform phase is washed with water, dried over $Na_2SO_4$ and concentrated to dryness.

Yield: 3.3 g, melting point: 127° C.
IR (in KBr): 1670 $cm^{-1}$
MS [m/e]: 274 (M+, 52%), 246 (3%), 206 (9%), 193 (100%), 151 (21%), 135 (9%), 122 (18%)

EXAMPLE 3

6-{5-[5-(1-Imidazolyl)-pentyl]-thien-2-yl}-3-oxo-2,3,4,5-tetrahydro-pyridazine 3.2 g of 4-{5-[5-(1-imidazolyl)-pentyl]-thien-2-yl}-4-oxo-butyric acid are suspended in 10 ml of water, 0.52 g of hydrazine hydrate are added and the mixture is stirred at 90° C. for 2 hours. After the mixture has been cooled, the precipitate formed is filtered off with suction, washed with water and dried.

Yield: 2.5 g, melting point: 114° C.

EXAMPLE 4

6-{5-[8-(1-Imidazolyl)-octyl]-thien-2-yl}-3-oxo-2,3,4,5-tetrahydro-pyridazine 1.8 g of 4-{5-[8-(1-Imidazolyl)-octyl]-thien-2-yl}-4-oxo-butyric acid are suspended in 10 ml of water, 0.26 g of hydrazine hydrate are added and the mixture is stirred at 90° C. for 2 hours. After the mixture has been cooled, the precipitate formed is filtered off with suction, washed with water and dried.

Yield: 0,6 g, melting point: 103° to 105° C.
IR (in KBr): 1690 $cm^{-1}$
MS (m/e): 358 (M+, 100%), 325 (69%), 288 (92%), 207 (11%), 193 (33%), 179 (17%), 165 (16%), 151 (34%), 137 (25%), 123 (33%), 109 (43%).

The following compounds are prepared analogously to Examples 1–4:

5. 6-{5-[3-(1-Imidazolyl)-propyl]-thien-2-yl}-3-oxo-2,3,4,5-tetrahydro-pyridazine,
6. 6-{5-[4-(1-Imidazolyl)-butyl]-thien-2-yl}-3-oxo-2,3,4,5-tetrahydro-pyridazine, 7. 6-{5-[6-(1-Imidazolyl)-hexyl]-thien-2-yl}-3-oxo-2,3,4,5-tetrahydro-pyridazine,
8. 6-{5-[7-(1-Imidazolyl)-heptyl]-thien-2-yl}-3-oxo-2,3,4,5-tetrahydro-pyridazine,
9. 6-{5-[8-(1-Imidazolyl)-octyl]-thien-2-yl}-3-oxo-2,3,4,5-tetrahydro-pyridazine,
10. 6-{5-[9-(1-Imidazolyl)-nonyl]-thien-2-yl}-3-oxo-2,3,4,5-tetrahydro-pyridazine,
11. 6-{5-[10-(1-Imidazolyl)-decyl]-thien-2-yl}-3-oxo-2,3,4,5-tetrahydro-pyridazine,
12. 6-{5-[11-(1-Imidazolyl)-undecyl]-thien-2-yl}-3-oxo-2,3,4,5-tetrahydro-pyridazine, and
13. 6-{5-[12-(1-Imidazolyl)-dodecyl]-thien-2-yl}-3-oxo-2,3,4,5-tetrahydro-pyridazine.

EXAMPLE 14

The fumaric acid salt of 6-[5-(1-imidazolylmethyl)-thien-2-yl]-3-oxo-2,3,4,5-tetrahydro-pyridazine A mixture of 1.5 g of 6-[5-(1-imidazolylmethyl)-thien-2-yl]-3-oxo-2,3,4,5-tetrahydro-pyridazine and 0.66 g of fumaric acid in 30 ml of ethanol is heated under reflux for about 30 minutes, until a clear solution has formed. When the solution is cooled, the salt crystallises out, and is filtered off with suction and dried.

Yield: 1.6 g, melting point: 182° C.

IR (in KBr): 1,670 cm$^{-1}$

Oxalates, succinates, malonates and the like and inorganic salts, such as hydrochlorides, hydrosulphates and the like can be prepared, for example, analogously to Example 14.

What we claim is:

1. 6-{5-[ω-(1-Imidazolyl)-alkyl]-thien-2-yl}-3-oxo-2,3,4,5-tetrahydro-pyridazines of the formula I

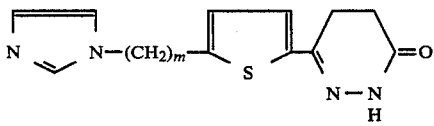

in which m denotes an integer from 1 to 12, and pharmaceutically acceptable acid addition salts thereof with inorganic or organic acids.

2. 6-[5-(1-Imidazolylmethyl)-thien-2-yl]-3-oxo-2,3,4,5-tetrahydro-pyridazine and pharmaceutically acceptable salts thereof.
3. 6-{5-[2-(1-Imidazolyl)-ethyl]-thien-2-yl}-3-oxo-2,3,4,5-tetrahydro-pyridazine and pharmaceutically acceptable salts thereof.
4. 6-{5-[3-(1-Imidazolyl)-propyl]-thien-2-yl}-3-oxo-2,3,4,5-tetrahydro-pyridazine and pharmaceutically acceptable salts thereof.
5. 6-{5-[4-(1-Imidazolyl)-butyl]-thien-2-yl}-3-oxo-2,3,4,5-tetrahydro-pyridazine and pharmaceutically acceptable salts thereof.
6. 6-{5-[5-(1-Imidazolyl)-pentyl]-thien-2-yl}-3-oxo-2,3,4,5-tetrahydro-pyridazine and pharmaceutically acceptable salts thereof.
7. 6-{5-[6-(1-Imidazolyl)-hexyl]-thien-2-yl}-3-oxo-2,3,4,5-tetrahydro-pyridazine and pharmaceutically acceptable salts thereof.
8. 6-{5-[7-(1-Imidazolyl)-heptyl]-thien-2-yl}-3-oxo-2,3,4,5-tetrahydro-pyridazine and pharmaceutically acceptable salts thereof.
9. 6-{5-[8-(1-Imidazolyl)-octyl]-thien-2-yl}-3-oxo-2,3,4,5-tetrahydro-pyridazine and pharmaceutically acceptable salts thereof.
10. 6-{5-[9-(1-Imidazolyl)-nonyl]-thien-2-yl}-3-oxo-2,3,4,5-tetrahydro-pyridazine and pharmaceutically acceptable salts thereof.
11. 6-{5-[10-(1-Imidazolyl)-decyl]-thien-2-yl}-3-oxo-2,3,4,5-tetrahydro-pyridazine and pharmaceutically acceptable salts thereof.
12. 6-{5-[11-(1-Imidazolyl)-undecyl]-thien-2-yl}-3-oxo-2,3,4,5-tetrahydro-pyridazine and pharmaceutically acceptable salts thereof.
13. 6-{5-[12-(1-Imidazolyl)-dodecyl]-thien-2-yl}-3-oxo-2,3,4,5-tetrahydro-pyridazine and pharmaceutically acceptable salts thereof.
14. Process for the treatment of inflammatory, atherosclerotic and thrombo-embolic illnesses in humans wherein between 1 to 500 mg per dose of a compound as claimed in any of claims 1 to 13 are administered to the human being suffering from such an inflammatory, atherosclerotic and/or thrombo-embolic illness one or several times daily.
15. Process as claimed in claim 14 wherein between 1 and 500 mg per dose of the active compound are administered two to three times daily.

* * * * *